US00PP08886P

United States Patent [19]

Klemm

[11] Patent Number: Plant 8,886

[45] Date of Patent: Sep. 6, 1994

[54] GERANIUM NAMED KLEUGUDO

[75] Inventor: Siegfried Klemm, Stuttgart, Fed. Rep. of Germany

[73] Assignee: Klemm & Sohn, Stuttgart-Muhlhausen, Fed. Rep. of Germany

[21] Appl. No.: 172,437

[22] Filed: Dec. 23, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Tilton, Fallon, Lungmus & Chestnut

[57] ABSTRACT

A new Geranium cultivar particularly distinguished by its very round and strong umbels with long lasting double petals of a orange color, having abundant dark foliage and compact growth.

1 Drawing Sheet

BACKGROUND OF THE NEW PLANT

The present invention comprises a new and distinct cultivar of Geranium, botanically known as *Pelargonium zonale-hybride.* The new cultivar is propagated from cuttings resulting from the cross of Drago and E 168 orange. Drago is a orange colored geranium having a double flower shape but not very broad petals. Drago's flower shape is fluffy and disorderly because of the small petals and many petaloids. E 168 is a seedling of the E-Generation of our planned breeding program and is not commercially available. E 168 is not known by any other synonyms. E 168 had a clear cup-shaped orange flower without petaloids and with broad petals. As a result of this cross the present cultivar was created in 1989 in Stuttgart, Germany and has been repeatedly asexually reproduced by cuttings in Stuttgart, Germany and Teneriffe, Italy over a four year period. It has been found to retain its distinctive characteristics through successive propagations and this novelty appears to be firmly fixed.

The new cultivar is distinguished from other pink varieties in that it has orange colored petals and nearly black foliage. The present cultivar has very dark leaves with zonation. It grows slowly but is compact and bushy. When it starts to bloom there are only florets open to a few clusters. These florets keep long on the plant. The orange florets stand in good contrast to the foliage.

DESCRIPTION OF THE DRAWING

This new Geranium plant is illustrated by the accompanying photographic drawing which shows blooms, buds, and foliage of the plant in full color, the color shown being as true as can be reasonably obtained by conventional photographic procedures.

DESCRIPTION OF THE NEW CULTIVAR

The following detailed descriptions set forth the distinctive characteristics of this new Geranium. The data which defines these characteristics was collected from asexual reproductions carried out in Stuttgart, Germany. The plant history was taken on 10 week old plants, blossomed under natural light in a greenhouse. Color readings were taken in the greenhouse under ambient light. Color references are primarily to The R.H.S. Colour Chart of The Royal Horticultural Society of London.

THE PLANT

Classification:

*Botanical.*—*Pelargonium zonale-hybride.*

*Commercial.*—Zonal Geranium.

Parentage:

*Seed parent.*—Drago, which is a seedling from our D-generation of plants.

*Pollen parent.*—E-168, which is a seedling from our E-generation of plants.

Form: High centered bush.

Shape: Round.

Height: 150–180 mm in June and 270–310 mm in September.

Stem length: 150–270 mm depending on the season.

Number of stems per stalk: 8.

Number of stalks per plant: 9.

Internode length: About 5–10 mm depending on the light where the plant is propagated.

Growth rate: If propagated in January the blooms can be sold in April.

Strength: Good cutting producer for propagation, and the plant performs very well after shipping as a rooted or unrooted cutting.

Foliage:

*Quantity.*—Many robust leaves.

*Size.*—80×70 mm.

*Shape.*—Round.

*Margin.*—Bicrenate.

*Texture.*—Smooth.

*Ribs and veins.*—None.

*Color.*—Upper side: Green — RHS 147-A and darker. The center is lighter than the zonation. Under side: Green — RHS 137-B.

Length of leaf stem: About 40–60 mm.

THE BUD

Size:

*Diameter.*—About 7–8 mm.

*Length.*—About 11–12 mm.

Shape: Elliptical.

Form: Pointed.

Rate of opening: Medium.

Color: When sepals first divide, the outer side (reverse side) is visible which is red-orange — RHS 40-B. When petals begin to unfurl the inside is visible, which is is orange — RHS 41-A.

Sepals:

*Number.*—5.

*Shape.*—Long and pointed.

*Color.*—Inside — glossy light green-RHS 146-B and light brown at the base RHS 183-C to green 146-C. Outside — green RHS 147-B and red-brown at the base RHS 187-B.

*Form.*—Standing up.

Petiole of floret:

*Length.*—20–23 mm.

*Strength.*—Very strong and a little thick arranged hemispherically around the end of the cluster stalk.

*Color.*—A greenish brown — RHS 176-B.

THE FLOWER

Blooming habit: Kleugudo starts with a few clusters in April and then blooms continuously until a frost.

Size: Approximately 51 mm×4 mm in diameter.

Borne: In a cluster having between about 42–89 florets per cluster.

Form: Cup.

Petals:

*Number.*—About eight per floret. Between 175–223 clusters on 3 plants in one season (April–September) or about 60 to 70 clusters per plant per season.

*Arrangement.*—Imbricated.

*Form.*—Medium broad.

*Color.*—Outer petals: The body is Indian orange RHS 32-A. The base is a little darker. Inside petal: The body is Capsicum red RHS 33-A. The base is a little darker. Reverse side: Mandarin and Poppy red RHS 40 C-D.

Texture: Soft.

Appearance: Satiny.

How long do petals remain on stem: About five-seven days depending on the weather.

Petaloids:

*Number.*—About 1 to 3.

*Size.*—About 4–11 mm.

*Color.*—Indian orange RHS 32-A.

Persistence: Matured florets or clusters should be picked off.

Disease resistance: Kleugudo does not suffer from Botrytis.

Weather resistance: Kleugudo is not unusually affected by wet or hot weather.

Lasting quality:

*On the plant.*—About 28 days.

*As a cut flower.*—About 8 days.

Fragrance: No perceptible fragrance.

REPRODUCTIVE ORGANS

Stamens:

*Anthers.*—Seven positioned around the ovaries with 1.9 mm length.

*Filaments.*—6 mm in length and white and red color.

Pollen: Dark orange in color.

Pistils:

*Number.*—One.

*Length.*—Approximately 7 mm.

*Stigmas.*—Red in color.

Ovaries: Green in color.

Seed: Fertile.

*Shape.*—Ovoid.

*Color at maturity.*—RHS 160-A with brown stripes.

I claim:

1. A new and distinct Geranium cultivar substantially as herein shown and described, particularly distinguished by its very round and strong umbels with long lasting double petals of an orange color, having abundant dark foliage and compact growth.

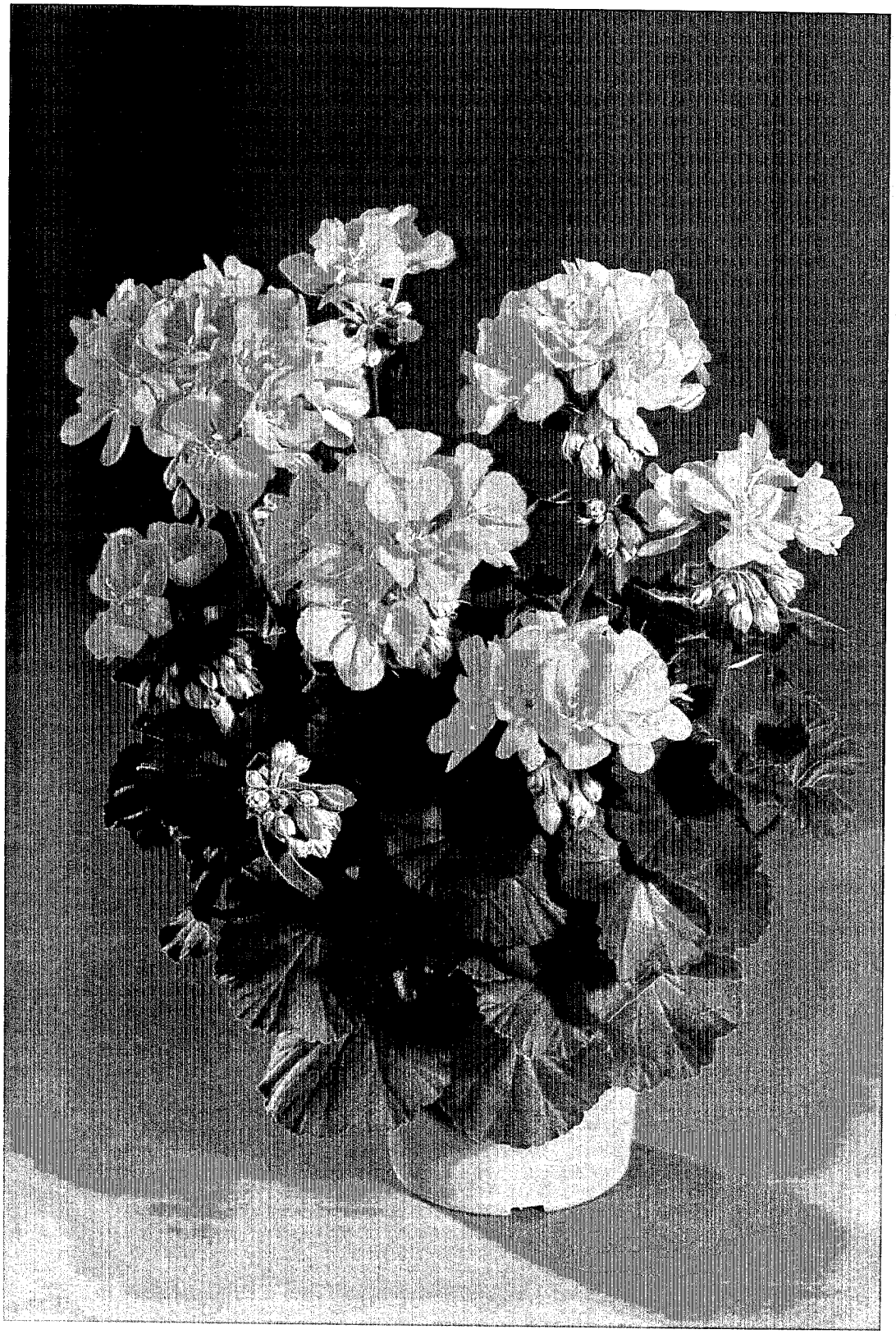

* * * * *